US009265708B2

(12) United States Patent
Yumioka et al.

(10) Patent No.: US 9,265,708 B2
(45) Date of Patent: Feb. 23, 2016

(54) LIQUID CLEANSER COMPRISING STEROL ESTER AND C5-6 HYDROXYALCOHOL

(71) Applicant: AJINOMOTO CO., INC., Tokyo (JP)

(72) Inventors: Rina Yumioka, Kawasaki (JP); Eiko Oshimura, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/664,958

(22) Filed: Mar. 23, 2015

(65) Prior Publication Data

US 2015/0190328 A1 Jul. 9, 2015

Related U.S. Application Data

(63) Continuation of application No. PCT/JP2013/075542, filed on Sep. 20, 2013.

(30) Foreign Application Priority Data

Sep. 24, 2012 (JP) ................. 2012-209724

(51) Int. Cl.
| | | |
|---|---|---|
| C11D 1/29 | (2006.01) | |
| C11D 1/90 | (2006.01) | |
| C11D 1/94 | (2006.01) | |
| A61K 8/63 | (2006.01) | |
| A61K 8/34 | (2006.01) | |
| A61K 8/37 | (2006.01) | |
| A61K 8/44 | (2006.01) | |
| A61K 8/46 | (2006.01) | |
| A61Q 5/02 | (2006.01) | |
| A61Q 19/10 | (2006.01) | |
| A61K 8/06 | (2006.01) | |
| A61K 8/86 | (2006.01) | |
| A61Q 5/12 | (2006.01) | |

(52) U.S. Cl.
CPC . *A61K 8/63* (2013.01); *A61K 8/062* (2013.01); *A61K 8/34* (2013.01); *A61K 8/345* (2013.01); *A61K 8/37* (2013.01); *A61K 8/375* (2013.01); *A61K 8/44* (2013.01); *A61K 8/442* (2013.01); *A61K 8/463* (2013.01); *A61K 8/86* (2013.01); *A61Q 5/02* (2013.01); *A61Q 5/12* (2013.01); *A61Q 19/10* (2013.01); *A61K 2800/49* (2013.01); *A61K 2800/52* (2013.01); *A61K 2800/596* (2013.01)

(58) Field of Classification Search
CPC ............. C11D 1/29; C11D 1/90; C11D 1/94; C11D 3/2044; C11D 11/0023
See application file for complete search history.

(56) References Cited

U.S. PATENT DOCUMENTS

| | | | |
|---|---|---|---|
| 2005/0112157 A1 | 5/2005 | Ruppert et al. | |
| 2013/0116340 A1* | 5/2013 | Furukawa | A61K 8/891 514/772 |
| 2013/0177516 A1* | 7/2013 | Tamura | A61K 8/894 424/70.12 |
| 2013/0231403 A1* | 9/2013 | Denda | A61Q 19/00 514/785 |

FOREIGN PATENT DOCUMENTS

| | | |
|---|---|---|
| FR | 2 908 993 A1 | 5/2008 |
| JP | 2001-311099 A | 11/2001 |
| JP | 2005-15467 A | 1/2005 |
| JP | 2005-530718 A | 10/2005 |
| JP | 2010-222323 A | 10/2010 |
| WO | 2004/056336 A2 | 7/2004 |
| WO | 2008/064979 A2 | 6/2008 |

OTHER PUBLICATIONS

Supplementary Search Report dated Oct. 1, 2015 issued in corresponding French patent application No. 1359164 (with English translation).

* cited by examiner

*Primary Examiner* — Charles Boyer

(74) *Attorney, Agent, or Firm* — Oblon, McClelland, Maier & Neustadt, L.L.P

(57) ABSTRACT

Provided is a composition containing a sterol ester, which is an oil poorly soluble in water, and superior in transparency, stability, foaming property, rinsability, skin feel (during rinsing and/or after use), and emollience. A composition containing (A) a sterol ester,
(B) one or more anionic surfactants selected from (B1) N-acylamino acid having a $C_{8-22}$ acyl group or a salt thereof, (B2) polyoxyethylene alkyl ether sulfate or a salt thereof,
(C) a betaine-type amphoteric surfactant,
(D) glyceryl mono-$C_{8-14}$ fatty acid ester,
(E) $C_{5-6}$ hydroxyalcohol, and
(F) water, and
having pH 4-8.

25 Claims, No Drawings

LIQUID CLEANSER COMPRISING STEROL ESTER AND C5-6 HYDROXYALCOHOL

CROSS REFERENCES TO RELATED APPLICATIONS

This application is a continuation of International Patent Application No. PCT/JP2013/075542, filed on Sep. 20, 2013, and claims priority to Japanese Patent Application No. 2012-209724, filed on Sep. 24, 2012, all of which are incorporated herein by reference in their entireties.

BACKGROUND OF THE INVENTION

1. Field of the Invention

The present invention relates to a composition containing (A) a sterol ester, (B) a particular anionic surfactant, (C) a betaine-type amphoteric surfactant, (D) glyceryl mono-$C_{8-14}$ fatty acid ester, (E) $C_{5-6}$ hydroxyalcohol and (F) water.

2. Discussion of the Background

Sterol ester is an oil having an emollient effect of "being absorbed well by skin and hair, and conferred smoothness and softness", and addition to liquid cleansers has been desired. Since sterol ester is poorly soluble in water, it is generally provided in the form of an emulsion wherein it is dispersed and stabilized in water. However, a sufficiently stable liquid cleanser cannot be easily obtained.

For example, patent document 1 proposes a technique for stably dispersing an oil phase comprising a liquid crystal in an aqueous phase mainly containing a foaming/cleansing ingredient, and patent document 2 proposes a technique for stabilizing an emulsion of an oily component in an aqueous solution of a foaming/cleansing ingredient. However, these techniques only afford a cloudy composition without transparency, which is less attractive visually for consumers, and its stability is not necessarily satisfactory. In addition, an oil may be solubilized in an aqueous phase by using a solvent such as ethanol. However, use of a volatile solvent causes problems of insufficient stability, low foaming/lathering property, friction during rinsing and insufficient emollient effect due to a decreased residual amount of a sterol ester on the skin or hair. While a nonionic surfactant with high HLB may also be used for solubilizing an oil in an aqueous phase, problems of decreased foaming/lathering property and rinsability and after-use stickiness of the skin or hair occur.

DOCUMENT LIST

Patent Documents patent document 1: JP-A-2001-311099
patent document 2: JP-A-2005-530718

SUMMARY OF THE INVENTION

Problems to be Solved by the Invention

An object of the present invention is to provide a composition containing a sterol ester, which is an oil poorly soluble in water, and superior in transparency, stability, foaming property, rinsability, skin feel (during rinsing and/or after use), and emollience.

Means of Solving the Problems

The present inventors have found that sterol ester can be solubilized in a cleanser by using a particular monofatty acid glyceryl and hydroxyalcohol as essential components, and found that a composition which is transparent and superior in stability, and shows good foaming property, superior emollience affording soft skin and hair due to residual sterol ester in the skin and hair after washing, and surprisingly, superior rinsability and silky skin/hair feel after use can be provided.

Accordingly, the present invention provides the following embodiments.

[1] A composition comprising
(A) a sterol ester,
(B) one or more anionic surfactants selected from (B1) N-acylamino acid having a $C_{8-22}$ acyl group or a salt thereof, (B2) polyoxyethylene alkyl ether sulfate or a salt thereof,
(C) a betaine-type amphoteric surfactant,
(D) glyceryl mono-$C_{8-14}$ fatty acid ester,
(E) $C_{5-6}$ hydroxyalcohol, and
(F) water, and
having pH 4.0-8.0.

[2] The composition of [1], wherein (A) is an N-acylamino acid sterol ester.

[3] The composition of [1] or [2], wherein (A) is an N-acylamino acid sterol ester represented by the formula (1):

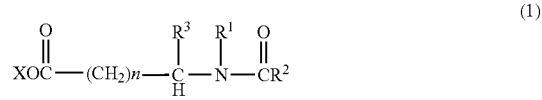

wherein
X is a hydrogen atom, an ester-forming residue of $C_{8-38}$ aliphatic alcohol, or an ester-forming residue of sterol,
$R^1$ is a hydrogen atom or a $C_{1-6}$ alkyl group,
$COR^2$ is a $C_{8-22}$ acyl group,
$R^3$ is a hydrogen atom or a group represented by —COOY wherein Y is a hydrogen atom, an ester-forming residue of $C_{8-38}$ aliphatic alcohol, or an ester-forming residue of sterol, and
n is 1 or 2,
provided that when $R^3$ is a hydrogen atom, then X is an ester-forming residue of sterol, and when $R^3$ is a group represented by —COOY, then at least one of X and Y is an ester-forming residue of sterol.

[4] The composition of [3], wherein the ester-forming residue of sterol is an ester-forming residue of phytosterol or cholesterol, $COR^2$ is a lauroyl group or a myristoyl group, and n is 2.

[5] The composition of [3], wherein the ester-forming residue of sterol is an ester-forming residue of phytosterol, $COR^2$ is a lauroyl group, and n is 2.

[6] The composition of any one of [1]-[4], wherein (A) is phytosteryl N-myristoyl-N-methyl-β-alaninate, di(cholesteryl/behenyl/2-octyldodecyl) N-lauroyl-L-glutamate, di(phytosteryl/behenyl/2-octyldodecyl) N-lauroyl-L-glutamate, di(cholesteryl/2-octyldodecyl) N-lauroyl-L-glutamate, di(phytosteryl/2-octyldodecyl) N-lauroyl-L-glutamate or di(phytosteryl/behenyl/2-octyldodecyl/isostearyl) N-lauroyl-L-glutamate.

[7] The composition of [1], wherein (A) is a fatty acid sterol ester.

[8] The composition of [1] or [7], wherein (A) is selected from the group consisting of phytosteryl butyrate, phytosteryl nonanoate, cholesteryl stearate, cholesteryl isostearate, phytosteryl isostearate, cholesteryl hydroxystearate, phytosteryl hydroxystearate, phytosteryl caprylate/caprate, phytosteryl linoleate, phytosteryl linolenate, phytosteryl ricinoleate, cholesteryl oleate, phytosteryl oleate, dihydrocholesteryl oleate, branched fatty acid ($C_{12-31}$) phytosteryl ester, phytosteryl canola oil fatty acid glycerides, phytosteryl rapeseed glycerides, jojoba oil fatty acid phytosteryl ester, Macadamia nut oil fatty acid phytosteryl ester, macadamia nut oil fatty acid cholesteryl ester, macadamia nut oil fatty acid dihydrocholesteryl ester, sunflower seed oil fatty acid phytosteryl ester, rice bran oil fatty acid phytosteryl ester, phytosteryl/isostearyl/cetyl/stearyl/behenyl dimer dilinoleate, bis-behenyl/isostearyl/phytosteryl dimer dilinoleyl dimer dilinoleate, phytosteryl/behenyl dimer dilinoleate and phytosteryl isostearyl dimer dilinoleate.

[9] The composition of any one of [1]-[8], wherein (B1) is N-acylamino acid represented by the formula (2):

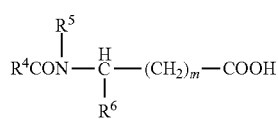

(2)

wherein
$R^4CO$ is a $C_{8-22}$ acyl group,
$R^5$ is a hydrogen atom or a $C_{1-6}$ alkyl group,
$R^6$ is a hydrogen atom, a $C_{1-6}$ alkyl group optionally substituted by a hydroxyl group, or a carboxyl group, and
m is an integer of 0-2, or a salt thereof.

[10] The composition of any one of [1]-[9], wherein (C) is an amide betaine-type amphoteric surfactant represented by the formula (4):

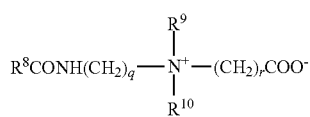

(4)

wherein
$R^8CO$ is a $C_{8-24}$ acyl group, $R^9$ and $R^{10}$ are each independently a hydrogen atom or a $C_{1-6}$ alkyl group,
q is an integer of 2-4, and
r is an integer of 1-3.

[11] The composition of any one of [1]-[10], wherein (D) is glyceryl monocaprylate.
[12] The composition of any one of [1]-[11], wherein (E) is 2-hydroxy-1-pentanol.
[13] The composition of any one of [1]-[12], wherein (A) is contained in 0.02-5 mass % relative to the total amount of (A)-(F).
[14] The composition of any one of [1]-[13], wherein (B) is contained in 2-35 mass % relative to the total amount of (A)-(F).
[15] The composition of any one of [1]-[14], wherein (C) is contained in 0.2-20 mass % relative to the total amount of (A)-(F).
[16] The composition of any one of [1]-[15], wherein (D) is contained in 0.1-10 mass % relative to the total amount of (A)-(F).
[17] The composition of any one of [1]-[16], wherein (E) is contained in 0.1-10 mass % relative to the total amount of (A)-(F).
[18] The composition of any one of [1]-[17], wherein mass of (A)/mass of (D) is 0.002-5.0.
[19] The composition of any one of [1]-[18], wherein mass of (A)/mass of (E) is 0.002-5.0.
[20] The composition of any one of [1]-[19], wherein mass of (A)/(mass of (D)+mass of (E)) is 0.001-2.5.
[21] The composition of any one of [1]-[20], wherein (mass of (D)+mass of (E))/(mass of (B)+mass of (C)) is 0.003-5.0.
[22] The composition of any one of [1]-[21], which is a liquid cleanser for skin or hair.
[23] A method of stabilizing a composition comprising a sterol ester, a surfactant and water, comprising mixing glyceryl mono-$C_{8-14}$ fatty acid ester and $C_{5-6}$ hydroxyalcohol.
[24] A method of solubilizing a sterol ester in a composition comprising a surfactant and water, comprising mixing glyceryl mono-$C_{8-14}$ fatty acid ester and $C_{5-6}$ hydroxyalcohol.

Effect of the Invention

According to the present invention, a composition wherein a sterol ester affording a superior skin care and hair care effect is dissolved at a high concentration without impairing transparency, which composition is superior in stability, foaming property, rinsability, skin feel (during rinsing and/or after use), and emollience, can be provided.

DETAILED DESCRIPTION OF THE PREFERRED EMBODIMENTS

[Component A: Sterol Ester]

Examples of the sterol ester include an N-acylamino acid sterol ester obtained by esterification of sterol with acylamino acid, a fatty acid sterol ester obtained by esterification of sterol with fatty acid and the like.

Examples of the sterol include phytosterols such as campesterol, campestanol, brassicasterol, 22-dehydrocampesterol, stigmasterol, stigmastanol, 22-dihydrospinasterol, 22-dehydrostigmastanol, 7-dehydrostigmasterol, sitosterol, tirucallol, euphol, fucosterol, isofucosterol, codisterol, clionasterol, poriferasterol, clerosterol, 22-dehydroclerosterol, fungi sterol, chondrillasterol, avenasterol, vernosterol, pollinastanol and the like; animal-derived sterols such as cholesterol, dihydrocholesterol, cholestanol, coprostanol, epicoprosterol, epicoprostanol, 22-dehydrocholesterol, desmosterol, 24-methylenecholesterol, lanosterol, 24,25-dihydrolanosterol, norlanosterol, spinasterol, dihydroagnosterol, agnosterol, lophenol, lathosterol and the like; fungal sterols such as dehydroergosterol, 22,23-dihydroergosterol, episterol, ascosterol, fecosterol and the like; and the like; hydrogenated products thereof, blended products thereof and the like. A mixture of sterol obtained by extraction from plant and the like may also be used.

As sterol, phytosterol, lanosterol, cholesterol or dihydrocholesterol is preferable, and phytosterol is more preferable. It is more preferable to use phytosterol including sitosterol, stigmasterol, campesterol and brassicasterol.

It is preferable that the ratio of sitosterol, stigmasterol, campesterol and brassicasterol (sitosterol:stigmasterol:campesterol:brassicasterol) be 25-65:10-45:5-30:0.01-10, more preferably 35-55:20-35:10-25:0.1-8.

Examples of the amino acid of acylamino acid include glycine, N-methylglycine, alanine, β-alanine, N-methyl-β-alanine, valine, leucine, isoleucine, serine, threonine, phenylalanine, tyrosine, tryptophan, cystine, cysteine, methionine, proline, hydroxyproline, asparagine, aspartic acid, glutamine, glutamic acid, arginine, histidine, lysine and the like. Of these, alanine, β-alanine, N-methyl-β-alanine, glutamic acid are preferable, N-methyl-β-alanine, glutamic acid are more preferable, glutamic acid are still more preferable Sterol ester is preferably an N-acylamino acid sterol ester, and an N-acylamino acid sterol ester represented by the formula (1) is particularly preferable.

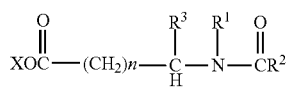

(1)

wherein
X is a hydrogen atom, an ester-forming residue of $C_{8-38}$ aliphatic alcohol, or an ester-forming residue of sterol,
$R^1$ is a hydrogen atom or a $C_{1-6}$ alkyl group,
$COR^2$ is a $C_{8-22}$ acyl group,
$R^3$ is a hydrogen atom or a group represented by —COOY wherein Y is a hydrogen atom, an ester-forming residue of $C_{8-38}$ aliphatic alcohol, or an ester-forming residue of sterol, and
n is 1 or 2,
provided that when $R^3$ is a hydrogen atom, then X is an ester-forming residue of sterol, and when $R^3$ is a group represented by —COOY, then at least one of X and Y is an ester-forming residue of sterol.

Examples of the "$C_{8-38}$ aliphatic alcohol" of the "ester-forming residue of $C_{8-38}$ aliphatic alcohol" for X or Y include monovalent $C_{8-38}$ aliphatic alcohol which is natural or synthetic, straight chain or branched chain, and saturated or unsaturated, which is exemplified by straight chain saturated alcohols such as caprylic alcohol, lauryl alcohol, myristyl alcohol, cetyl alcohol, stearyl alcohol, arachidyl alcohol, behenyl alcohol and the like; branched chain saturated alcohols such as 2-hexyldecyl alcohol, 2-octyldodecyl alcohol, isostearyl alcohol, decyltetradecyl alcohol and the like; straight chain unsaturated alcohols such as oleyl alcohol, linoleyl alcohol and the like; and the like.

The "$C_{8-38}$ aliphatic alcohol" of the "ester-forming residue of $C_{8-38}$ aliphatic alcohol" for X or Y is preferably $C_{8-30}$ aliphatic alcohol (preferably $C_{12-24}$ aliphatic alcohol, more preferably $C_{16-20}$ aliphatic alcohol) which has a melting point of not less than 25° C. Preferable specific examples include branched chain saturated alcohol such as 2-hexyldecyl alcohol, 2-octyldodecyl alcohol, isostearyl alcohol, decyltetradecyl alcohol and the like; and straight chain unsaturated alcohol such as oleyl alcohol, linoleyl alcohol and the like. Of these, 2-hexyldecyl alcohol, 2-octyldodecyl alcohol and decyltetradecyl alcohol are preferable, and 2-octyldodecyl alcohol is more preferable.

In another embodiment, the "$C_{8-38}$ aliphatic alcohol" of the "ester-forming residue of $C_{8-38}$ aliphatic alcohol" for X or Y is preferably saturated $C_{12-38}$ aliphatic alcohol (preferably $C_{12-24}$ aliphatic alcohol, more preferably $C_{16-22}$ aliphatic alcohol) which has a melting point of less than 25° C.

Preferable specific examples include cetyl alcohol, stearyl alcohol, behenyl alcohol and the like. Of these, stearyl alcohol and behenyl alcohol are preferable, and behenyl alcohol is more preferable.

Examples of the "sterol" of the "ester-forming residue of sterol" for X or Y include the aforementioned sterols. Of those, phytosterol, lanosterol, cholesterol and dihydrocholesterol are preferable, phytosterol and cholesterol are more preferable, and phytosterol is further preferable. Use of phytosterol containing sitosterol, stigmasterol, campesterol and brassicasterol is more preferable.

The ratio of sitosterol, stigmasterol, campesterol and brassicasterol, sitosterol:stigmasterol:campesterol:brassicasterol, is preferably 25-65:10-45:5-30:0.01-10, more preferably 35-55:20-35:10-25:0.1-8.

As $R^3$, a group represented by —COOY is preferable.

Examples of the "$C_{8-22}$ acyl group" for $COR^2$ include acyl groups derived from straight chain or branched chain, saturated or unsaturated $C_{8-22}$ fatty acid, which is exemplified by octanoyl, nonanoyl, decanoyl, undecanoyl, lauroyl, myristoyl, palmitoyl, stearoyl, oleoyl, linoleyl and the like. It may be an acyl group derived from fatty acid having a single composition, as well as an acyl group derived from a naturally occurring mixed fatty acid such as coconut oil fatty acid, castor oil fatty acid, olive oil fatty acid, palm oil fatty acid and the like, or fatty acid (including branched fatty acid) obtained synthetically. Of these, lauroyl, myristoyl, palmitoyl and stearoyl are preferable, lauroyl and myristoyl are more preferable, and lauroyl is particularly preferable.

That is, $R^2$ of $COR^2$ is a straight chain or branched chain, saturated or unsaturated $C_{7-21}$ hydrocarbon group. Examples of the $C_{7-21}$ hydrocarbon group include a $C_{7-21}$ alkyl group and a $C_{7-21}$ alkenyl group.

Examples of the "$C_{7-21}$ alkyl group" include heptyl, octyl, nonyl, decyl, undecyl, dodecyl (lauryl), tridecyl, tetradecyl (myristyl), pentadecyl, hexadecyl (palmityl, cetyl), heptadecyl, octadecyl (stearyl), nonadecyl, icosyl (arachidyl) and the like. Of these, an alkyl group having 11-13 carbon atoms is preferable.

The "$C_{7-21}$ alkenyl group" may be a straight chain or branched chain and, for example, 1-heptenyl, 1-octenyl, 1-nonenyl, 1-decenyl, 1-unedecenyl, 1-dodecenyl, 1-triecenyl, 1-tetradecenyl, 1-pentadecenyl, 1-hexadecenyl, 1-heptadecenyl, 1-octadecenyl, 1-nonadecenyl, 1-icosenyl, 1-henicosenyl and the like can be mentioned. Of these, an alkenyl group having 11-13 carbon atoms is preferable.

Examples of the "$C_{1-6}$ alkyl group" for $R^1$ include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl and the like. Of these, methyl and ethyl are preferable.

As $R^1$, a hydrogen atom is preferable.

n is 1 or 2. When n is 1 and $R^3$ is —COOY, the N-acylamino acid sterol ester is an N-acylaspartic acid sterol ester, and when n is 2 and $R^3$ is —COOY, it is an N-acylglutamic acid sterol ester. When n is 2 and $R^3$ is —COOY, i.e. an N-acylglutamic acid sterol ester is preferable. The amino acid may be any of an optically active form and a racemate.

In the present invention, the N-acylamino acid sterol ester may be a mixture of two or more kinds.

As the N-acylamino acid sterol ester, phytosteryl N-myristoyl-N-methyl-β-alaninate, di(cholesteryl/behenyl/2-octyldodecyl) N-lauroyl-L-glutamate, di(phytosteryl/behenyl/2-octyldodecyl) N-lauroyl-L-glutamate, di(cholesteryl/2-octyldodecyl) N-lauroyl-L-glutamate, di(phytosteryl/2-octyldodecyl) N-lauroyl-L-glutamate or di(phytosteryl/behenyl/2-octyldodecyl/isostearyl) N-lauroyl-L-glutamate is preferable, di(cholesteryl/behenyl/2-octyldodecyl) N-lauroyl-L-glutamate, di(phytosteryl/behenyl/2-octyldodecyl) N-lauroyl-L-glutamate, di(cholesteryl/2-octyldodecyl) N-lauroyl-L-glutamate or di(phytosteryl/2-octyldodecyl) N-lauroyl-L-glutamate is more preferable, di(phytosteryl/behenyl/2-octyldodecyl) N-lauroyl-L-glutamate or di(phytosteryl/2-octyldodecyl) N-lauroyl-L-glutamate is preferable, and di(phytosteryl/2-octyldodecyl) N-lauroyl-L-glutamate is more preferable.

Indication of di(phytosteryl/2-octyldodecyl) N-lauroyl-L-glutamate in the present specification means a mixture of compounds obtained by ester formation of two carboxy groups of N-lauroyl-L-glutamic acid with phytosterol, or phytosterol and 2-octyldodecyl alcohol. That is, it contains N-lauroyl-L-glutamic acid diphytosteryl ester, N-lauroyl-L-glutamic acid γ-phytosteryl-α-2-octyldodecyl ester and N-lauroyl-L-glutamic acid α-phytosteryl-γ-2-octyldodecyl ester.

In addition, indication of di(phytosteryl/behenyl/2-octyldodecyl) N-lauroyl-L-glutamate means a mixture of compounds obtained by ester formation of two carboxyl groups of N-lauroyl-L-glutamic acid with phytosterol, phytosterol and behenyl alcohol, and phytosterol and 2-octyldodecyl alcohol. That is, it contains N-lauroyl-L-glutamic acid diphytosteryl ester, N-lauroyl-L-glutamic acid γ-phytosteryl-α-2-octyldodecyl ester, N-lauroyl-L-glutamic acid α-phytosteryl-γ-2-octyldodecyl ester and N-lauroyl-L-glutamic acid γ-phytosteryl-α-behenyl ester and N-lauroyl-L-glutamic acid α-phytosteryl-γ-behenyl ester.

That is, the above-mentioned N-lauroyl-L-glutamic acid sterol ester is a mixture of compounds obtained by ester formation of two carboxyl groups of N-lauroyl-L-glutamic acid with phytosterol (cholesterol) or phytosterol (cholesterol) and $C_{8-38}$ aliphatic alcohol.

As the sterol ester, a fatty acid sterol ester esterified with sterol and fatty acid can also be used. Examples of the fatty acid include one or more kinds of straight chain or branched chain, saturated or unsaturated $C_{4-31}$ fatty acids such as butyric acid, valeric acid, caproic acid, caprylic acid, nonanoic acid, capric acid, lauric acid, myristic acid, palmitic acid, pulmitoleic acid, stearic acid, hydroxystearic acid, isostearic acid, arachidic acid, behenic acid, lignoceric acid, cerotic acid, oleic acid, linoleic acid, linolenic acid, ricinoleic acid, arachidonic acid, eicosapentaenoic acid, docosapentaenoic acid, docosahexaenoic acid, nervonic acid and the like. These may also be derived from naturally occurring plant and animal oils. Examples thereof include castor oil fatty acid, dehydrogenated castor oil fatty acid, macadamia nut oil fatty acid, coconut oil fatty acid, peanut oil fatty acid, fish oil fatty acid, rape seed oil fatty acid (canola oil fatty acid), hybrid sunflower oil fatty acid, sunflower oil fatty acid, sunflower seed oil fatty acid, palm oil fatty acid, cottonseed oil fatty acid, soybean oil fatty acid, safflower oil fatty acid, wheat germ oil fatty acid, rice bran oil fatty acid, sesame oil fatty acid, corn oil fatty acid, evening primrose seed oil fatty acid, lanolin fatty acid, non-hydroxylanolin fatty acid, hydroxylanolin fatty acid, milk fat fatty acid and the like. These fatty acids may also be hydrogenated. They may also be dimer acids (e.g., dimer dilinoleate) which are dibasic acids obtained by molecular polymerization of unsaturated fatty acids. Among these, butyric acid, nonanoic acid, stearic acid, isostearic acid, hydroxystearic acid, caprylic acid, capric acid, ricinoleic acid, oleic acid, macadamia nut oil fatty acid, sunflower seed oil fatty acid, rice bran oil fatty acid, and dimer dilinoleate are preferable, macadamia nut oil fatty acid and dimer dilinoleate are more preferable, and dimer dilinoleate is further preferable.

Examples of the fatty acid sterol ester obtained by esterification of sterol with a fatty acid include phytosteryl butyrate, phytosteryl nonanoate, cholesteryl stearate, cholesteryl isostearate, phytosteryl isostearate, cholesteryl hydroxystearate, phytosteryl hydroxystearate, phytosteryl caprylate/caprate, phytosteryl linoleate, phytosteryl linolenate, phytosteryl ricinoleate, cholesteryl oleate, phytosteryl oleate, dihydrocholesteryl oleate, branched fatty acid ($C_{12-31}$) phytosteryl ester, phytosteryl canola oil fatty acid glycerides, phytosteryl rapeseed glycerides, jojoba oil fatty acid phytosteryl ester, macadamia nut oil fatty acid phytosteryl ester, macadamia nut oil fatty acid cholesteryl ester, macadamia nut oil fatty acid dihydrocholesteryl ester, sunflower seed oil fatty acid phytosteryl ester, rice bran oil fatty acid phytosteryl ester, phytosteryl/isostearyl/cetyl/stearyl/behenyl dimer dilinoleate, bis-behenyl/isostearyl/phytosteryl dimer dilinoleyl dimer dilinoleate, phytosteryl/behenyl dimer dilinoleate and phytosteryl isostearyl dimer dilinoleate and the like. Preferred are macadamia nut oil fatty acid phytosteryl ester, phytosteryl/isostearyl/cetyl/stearyl/behenyl dimer dilinoleate, bis-behenyl/isostearyl/phytosteryl dimer dilinoleyl dimer dilinoleate, phytosteryl/behenyl dimer dilinoleate and phytosteryl isostearyl dimer dilinoleate.

The composition of the present invention can contain one or more kinds of sterol esters.

In the composition of the present invention, (A) is not particularly limited. The amount thereof to be used is preferably 0.02-5 mass % relative to the total amount of (A)-(F). The lower limit is more preferably 0.05 mass %, further preferably 0.07 mass %, and still more preferably 0.1 mass. The upper limit is more preferably 3 mass, further preferably 2.5 mass %, further more preferably 2 mass %, and still more preferably 1 mass %.

[Component B: Anionic Surfactant]

(B) in the present invention is one or more anionic surfactants selected from (B1) N-acylamino acid having a $C_{8-22}$ acyl group and a salt thereof, (B2) polyoxyethylene alkyl ether sulfuric acid and a salt thereof.

The N-acylamino acid having a $C_{8-22}$ acyl group in (B1) can be obtained by, for example, Schotten-Baumann reaction of amino acid and fatty acid halide.

As the amino acid, glycine, N-methylglycine, alanine, β-alanine, N-methyl-β-alanine, threonine, glutamic acid, aspartic acid and the like can be used. These amino acids may be any of an L form, a D form and a DL form, or may also be a mixture of two or more kinds selected from these. Glycine, N-methylglycine, alanine, N-methyl-β-alanine, threonine and glutamic acid are preferable, since they can be easily added to a liquid cleanser and afford a good feeling of touch.

The N-acylamino acid having a $C_{8-22}$ acyl group is preferably a compound represented by the formula (2).

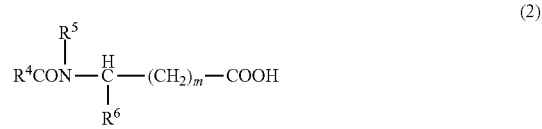

(2)

wherein
$R^4CO$ is a $C_{8-22}$ acyl group,
$R^5$ is a hydrogen atom or a $C_{1-6}$ alkyl group,
$R^6$ is a hydrogen atom, a $C_{1-6}$ alkyl group optionally substituted by a hydroxyl group, or a carboxyl group, and
m is an integer of 0-2.

As the "$C_{8-22}$ acyl group" in the N-acylamino acid having a $C_{8-22}$ acyl group and "$C_{8-22}$ acyl group" for $R^4CO$, a straight chain or branched chain $C_{8-22}$ acyl group derived from a saturated or unsaturated fatty acid having 8-22 carbon atoms can be used. Examples of the fatty acid include caprylic acid, capric acid, lauric acid, myristic acid, stearic acid, isostearic acid, palmitic acid, oleic acid, linoleic acid, behenic acid, coconut oil fatty acid, palm fatty acid, hydrogenated beef tallow fatty acid and the like. One kind of these may be used, or a mixture of two or more kinds selected from the above-mentioned group may be used. Particularly, coconut oil fatty acid, lauric acid and myristic acid are preferable since they easily generate foam with good quality.

That is, $R^4$ of $R^4CO$ is a straight chain or branched chain, saturated or unsaturated $C_{7-21}$ hydrocarbon group. Examples of the $C_{7-21}$ hydrocarbon group include a $C_{7-21}$ alkyl group and a $C_{7-21}$ alkenyl group.

Examples of the "$C_{7-21}$ alkyl group" include heptyl, octyl, nonyl, decyl, undecyl, dodecyl (lauryl), tridecyl, tetradecyl (myristyl), pentadecyl, hexadecyl (palmityl, cetyl), heptadecyl, octadecyl (stearyl), nonadecyl, icosyl (arachidyl) and the like. Of these, an alkyl group having 11-13 carbon atoms is preferable.

The "$C_{7-21}$ alkenyl group" may be a straight chain or branched chain. Examples thereof include 1-heptenyl, 1-octenyl, 1-nonenyl, 1-decenyl, 1-undecenyl, 1-dodecenyl, 1-tridecenyl, 1-tetradecenyl, 1-pentadecenyl, 1-hexadecenyl, 1-heptadecenyl, 1-octadecenyl, 1-nonadecenyl, 1-icosenyl, 1-henicosenyl and the like. Of these, an alkenyl group having 11-13 carbon atoms is preferable.

Examples of the "$C_{1-6}$ alkyl group" for $R^5$ include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, dimethylbutyl, 2-ethylbutyl and the like. Of these, methyl and ethyl are preferable, and ethyl is more preferable.

As $R^5$, a hydrogen atom is preferable.

Examples of the "$C_{1-6}$ alkyl group" for $R^6$ include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl and the like. Of these, methyl and ethyl are preferable. Examples of the "$C_{1-6}$ alkyl group" substituted by a hydroxy group include 2-hydroxyethyl and the like.

As $R^6$, a hydrogen atom, methyl or 2-hydroxyethyl is preferable.

While polyoxyethylene alkyl ether sulfuric acid in (B2) is not particularly limited, polyoxyethylene alkyl ether sulfuric acid represented by the formula (3) is preferable.

$$R^7\text{—}(OC_2H_4)_p\text{—}OSO_3H \quad (3)$$

wherein
$R^7$ is a $C_{8-24}$ alkyl group, and
p is $0.5 \leq p \leq 8$.

Examples of the "$C_{8-24}$ alkyl group" for $R^7$ include octyl, nonyl, decyl, undecyl, dodecyl (lauryl), tridecyl, tetradecyl (myristyl), pentadecyl, hexadecyl (palmityl, cetyl), heptadecyl, octadecyl (stearyl), nonadecyl, icosyl (arachidyl), docosyl (behenyl), tricosyl, tetracosyl and the like.

p is an average addition number of ethylene oxide and is $0.5 \leq p \leq 8$. The lower limit of p is preferably 1.0, more preferably 1.5, and further preferably 2.0. The upper limit is preferably 7.0, more preferably 5.0, further preferably 4.0, more preferably 3.5, and still more preferably 3.0.

Salts of N-acylamino acid having a $C_{8-22}$ acyl group of (B1) and polyoxyethylene alkyl ether sulfuric acid of (B2) are not particularly limited. Examples thereof include inorganic salts with alkali metal such as sodium, potassium and the like, alkaline earth metal such as calcium, magnesium and the like, aluminum, zinc and the like, and organic salts with organic amine such as ammonia, monoethanolamine, diethanolamine, triethanolamine and the like, basic amino acid such as arginine, lysine and the like. One kind of these may be used, or a mixture of two or more kinds selected from the above-mentioned group may be used. In view of easy availability, handling property and the like, alkali metal salt, organic amine salt and basic amino-acid salt are preferable, and sodium salt, potassium salt, triethanolamine salt and arginine salt are particularly preferable.

Examples of the N-acylamino acid having a $C_{8-22}$ acyl group or a salt thereof of (B1) include sodium cocoyl glutamate (coconut oil fatty acid acyl sodium glutamate), sodium lauroyl glutamate, and TEA-cocoyl glutamate (coconut oil fatty acid acylglutamic acid triethanolamine salt). Of these, sodium cocoyl glutamate is preferable.

As the polyoxyethylene alkyl ether sulfate or a salt thereof of (B2), polyoxyethylene lauryl ether sodium sulfate or polyoxyethylenelauryl ether ammonium sulfate is preferable, and polyoxyethylene lauryl ether sodium sulfate (sodium laureth sulfate) is more preferable.

In the composition of the present invention, while (B) is not particularly limited, it is preferably used in 2-35 mass % relative to the total amount of (A)-(F). When it is not less than 2 mass %, foaming property becomes better, and when it is not more than 35 mass %, the flowability of the composition becomes more preferable and the handling property thereof becomes more superior. Since a composition having sufficient washing property and suitable viscosity over a wide temperature range can be obtained, it is preferably 3-25 mass %, more preferably 5-20 mass %.

[Component C: Betaine-Type Amphoteric Surfactant]

While the betaine-type amphoteric surfactant of (C) to be used in the present invention is not particularly limited, an acetic acid betaine-type amphoteric surfactant, an amide betaine-type amphoteric surfactant, a sulfobetaine-type amphoteric surfactant, a phosphobetaine-type amphoteric surfactant, an imidazolinium betaine-type amphoteric surfactant and the like can be specifically used. Preferable examples of the betaine-type amphoteric surfactant include an amide betaine-type amphoteric surfactant represented by the formula (4).

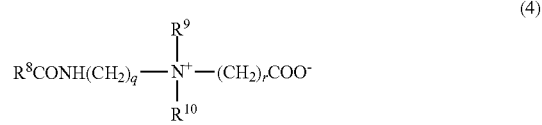

(4)

wherein
$R^8CO$ is a $C_{8-24}$ acyl group, $R^9$ and $R^{10}$ are each independently a hydrogen atom or a $C_{1-6}$ alkyl group,
q is an integer of 2-4, and
r is an integer of 1-3.

As the "$C_{8-24}$ acyl group" for $R^8CO$, a straight chain or branched chain $C_{8-24}$ acyl group derived from saturated or unsaturated fatty acid can be used. Examples of the fatty acid include caprylic acid, capric acid, lauric acid, myristic acid, stearic acid, isostearic acid, palmitic acid, pulmitoleic acid, oleic acid, linoleic acid, behenic acid, arachidonic acid, coconut oil fatty acid, palm fatty acid, hydrogenated beef tallow fatty acid and the like. One kind of these may be used, or a mixture of two or more kinds selected from the above-mentioned group may be used. Particularly, coconut oil fatty acid, lauric acid and myristic acid are preferable, since they easily generate foam with good quality.

That is, $R^8$ of $R^8CO$ is a straight chain or branched chain, saturated or unsaturated $C_{7-23}$ hydrocarbon group. Examples of the $C_{7-23}$ hydrocarbon group include a $C_{7-23}$ alkyl group and a $C_{7-23}$ alkenyl group.

Examples of the "$C_{7-23}$ alkyl group" include heptyl, octyl, nonyl, decyl, undecyl, dodecyl (lauryl), tridecyl, tetradecyl (myristyl), pentadecyl, hexadecyl (palmityl, cetyl), heptadecyl, octadecyl (stearyl), nonadecyl, icosyl (arachidyl), docosyl (behenyl), tricosyl and the like. Of these, an alkyl group having 11-13 carbon atoms is preferable.

The "$C_{7-23}$ alkenyl group" may be straight chain or branched chain. Examples thereof include a 1-heptenyl, 1-octenyl, 1-nonenyl, 1-decenyl, 1-undecenyl, 1-dodecenyl, 1-tridecenyl, 1-tetradecenyl, 1-pentadecenyl, 1-hexadecenyl, 1-heptadecenyl, 1-octadecenyl, 1-nonadecenyl, 1-icosenyl, 1-henicosenyl, 1-docosenyl, 1-tridocosenyl and the like. Of these, an alkenyl group having 11-13 carbon atoms is preferable.

Examples of the "$C_{1-6}$ alkyl group" for $R^9$ or $R^{10}$ include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl and the like. Of these, methyl and ethyl are preferable, and methyl is more preferable.

q is an integer of 2-4, preferably 3.

r is an integer of 1-3, preferably 1.

Preferable examples of (C) include lauric acid amide propyl betaine, coconut oil fatty acid amide propyl betaine (cocamidopropyl betaine), and myristic acid amide propyl betaine. In view of foaming property and stability of the composition, coconut oil fatty acid amide propyl betaine is particularly preferable.

In the composition of the present invention, while (C) is not particularly limited, it is preferably used in 0.2-20 mass % relative to the total amount of (A)-(F). When it is not less than 0.2 mass %, foam can be generated faster, and when it is not more than 20 mass %, form retention is further improved. In view of a good balance among fast foaming, foam volume and foam retention, 0.5-15 mass % is preferable, and 1.0-10 mass % is more preferable.

[Component D: Glyceryl Mono-$C_{8-14}$ Fatty Acid Ester]

Specific examples of (D) glyceryl mono-$C_{8-14}$ fatty acid ester to be used in the present invention include glyceryl monocaprylate, glyceryl monocapriate, glyceryl monolauriate and glyceryl monomyristiate. One kind of these may be used, or a mixture of two or more kinds selected from the above-mentioned group may be used. Glyceryl monocaprylate is particularly preferable.

In the composition of the present invention, while (D) is not particularly limited, it is preferably used in 0.1-10 mass % relative to the total amount of (A)-(F). When it is not less than 0.1 mass %, foaming property becomes better, and when it is not more than 10 masse, stability is further increased. It is preferably 0.5-8 mass %, more preferably 1-5 mass %, since the transparency of the composition is stably maintained from low temperature to high temperature.

[Component E: $C_{5-6}$ Hydroxyalcohol]

Specific examples of (E) $C_{5-6}$ hydroxyalcohol to be used in the present invention include 2-hydroxy-1-pentanol, 3-hydroxy-3-methylbutanol, 2,2-dimethyl-3-hydroxybutanol, 2-hydroxy-1-hexanol, 6-hydroxy-1-hexanol and the like. One kind of these may be used, or a mixture of two or more kinds selected from the above-mentioned group may be used. Of these, 2-hydroxy-1-pentanol, 2-hydroxy-1-hexanol and 6-hydroxy-1-hexanol are preferable, 2-hydroxy-1-pentanol is more preferable.

In the composition of the present invention, while (E) is not particularly limited, it is preferably used in 0.1-10 mass %, more preferably 0.5-8 mass %, further preferably 1-5 mass %, relative to the total amount of (A)-(F).

The composition of the present invention generally has pH 4-8, preferably 4.0-8.0. It is preferably 4.5-7.5, more preferably 4.8-7.2, particularly preferably 5.0-7.0.

The mass of (A)/mass of (D) is preferably 0.002-5.0. It is more preferably 0.005-2.0, still more preferably 0.01-1.5, further preferably 0.02-1.0.

The mass of (A)/mass of (E) is preferably 0.002-5.0. It is more preferably 0.005-2.0, still more preferably 0.01-1.5, further preferably 0.02-1.0.

The mass of (A)/(mass of (D)+mass of (E)) is preferably 0.001-2.5. It is more preferably 0.003-1.0, still more preferably 0.005-0.75, further preferably 0.01-0.5.

The (mass of (D)+mass of (E))/(mass of (B)+mass of (C)) is preferably 0.003-5.0. It is more preferably 0.01-3.0, still more preferably 0.03-1.5, further preferably 0.05-1.0.

The composition of the present invention is preferably "transparent". The "transparent" in the present specification means the absence of cloudiness due to emulsification of sterol ester in an aqueous phase. It may be cloudy due to the dispersion of solid components such as pearly sheen agent, organic or inorganic powder, solid surfactant and the like.

While the use of the composition of the present invention is not particularly limited, the composition can be provided as various cleansers and cosmetic agents (including quasi-drugs). Examples thereof include cleansing compositions such as soap, detergent, facial wash (cream, paste, liquid, gel, aerosol and the like), hair shampoo, body shampoo, shower gel and the like, mouth cavity compositions such as toothpaste etc., and the like. To utilize transparency of the form of the agent and emollient effect to the skin and hair, the form of a liquid cleanser for skin and hair is preferable.

The composition of the present invention can be applied to any animal such as human, animal other than human [e.g., mammals other than human (domestic animals and pets such as swine, bovine, horse, dog and the like, birds (poultry and pet such as turkey, chicken etc.) and the like] and the like.

The production method of the composition of the present invention is not particularly limited, and it may be a combination of known methods. For example, the composition can be produced by weighing all starting materials, mixing and dissolving them by heating to 70-90° C., and cooling them to room temperature with stirring.

The composition of the present invention can appropriately contain the aforementioned essential components, as well as various optional components used for general cosmetic agents, quasi-drugs and the like, as long as the effect of the present invention is not inhibited. Specific examples include components such as oil, surfactant, thickener, preservative, flavor, UV absorber, moisturizer, physiologically active component, antioxidant, anti-inflammatory agent, antibacterial agent, adiaphoretic, chelating agent, neutralizer, pH adjusting agent and the like, which can be added according to specific use and formulation.

Another embodiment of the present invention is a method for stabilizing a composition containing a sterol ester, a surfactant and water, comprising mixing glyceryl mono-$C_{8-14}$ fatty acid ester and $C_{5-6}$ hydroxyalcohol. The definitions thereof are the same as those in (A)-(E) mentioned above.

For example, the present invention provides a method of stabilizing a sterol ester or maintaining a transparent state free of clouding, which comprises mixing a composition containing (A) a sterol ester (1 part by mass), (B) a surfactant (1-150 parts by mass), (C) a surfactant (0.5-75 parts by mass) and water (100-1500 parts by mass) with (D) glyceryl mono-$C_{8-14}$ fatty acid ester (1-50 parts by mass) and (E) $C_{5-6}$ hydroxyalcohol (1-50 parts by mass), each relative to 1 part by mass of the sterol ester.

A still another embodiment of the present invention is a method for solubilizing a sterol ester in a composition containing a surfactant and water, which comprises mixing glyceryl mono-$C_{8-14}$ fatty acid ester and $C_{5-6}$ hydroxyalcohol. The definitions thereof are the same as those in (A)-(E) mentioned above.

Specifically, the present invention provides a method of solubilizing a sterol ester, comprising mixing (A) an sterol ester (1 part by mass), (B) a surfactant (1-150 parts by mass), (C) a surfactant (0.5-75 parts by mass), water (100-1500 parts by mass), (D) glyceryl mono-$C_{8-14}$ fatty acid ester (1-50 parts by mass) and (E) $C_{5-6}$ hydroxyalcohol (1-50 parts by mass), each relative to 1 part by mass of the sterol ester.

EXAMPLES

In the following, the present invention is explained in detail by referring to Examples, which are not to be construed as limitative.

Examples 1-16, Comparative Examples 1-14

Respective components of the compositions made of the blending compositions described in the below-mentioned Table 1-Table 3 were weighted, dissolved by mixing at 70-90° C., and cooled with stirring to room temperature, and the transparency, stability, foaming property, rinsing performance (quick rinsing), feeling of touch (no friction during rinsing, silky touch) and emollience (softness of skin after washing) were evaluated by the following methods.
(Transparency at 25° C.)

A composition was filled in a transparent glass bottle (diameter about 3.5 cm, volume 50 mL) while avoiding air bubbles, and left standing in a room at 25° C. overnight. White paper printed with a black alphabetic letter "A" (Times New Roman font, 20 point) was placed behind the bottle, and the letter was seen through the composition under the room light. The transparency was evaluated according to the following criteria.
⊙ Turbidity and oil separation were not observed and A was clearly seen.
○ Semi-transparent, A was clearly seen, oil separation was not observed.
Δ Turbidity was strong, A was blurred or the shape of the letter could not be recognized.
x Phase separation of oil was observed or oil drops with a size visible to naked eyes were dispersed.
(Stability at 40° C.)

A composition was filled in a transparent glass bottle (diameter about 3.5 cm, volume 50 mL), and left standing in a thermostatic tank at 40° C. for 1 month. The bottle was taken out from the thermostatic tank and transparency of the composition was immediately evaluated according to the above-mentioned criteria.
(Foaming Property)

A composition (1.0 g) was placed on the palm, a small amount of water was added, and foam was generated by mixing with the other hand for 30 seconds. The foam volume was evaluated by 5 panelists.
4: extremely large
3: large
2: normal
1: slightly less
0: less An average point of not less than 3.0 was marked with ⊙, not less than 2.0 and less than 3.0 with ○, not less than 1.0 and less than 2.0 with Δ, and less than 1.0 with x.
(Rinsability)

A composition (1.0 g) was foamed, spread over the whole both hands, and rinsed with a shower of tap water at 35-40° C. while rubbing hands therein. How fast the sliminess was removed was evaluated by 5 panelists.
4: extremely fast
3: fast
2: normal
1: rather slow
0: slow An average point of not less than 3.0 was marked with ⊙, not less than 2.0 and less than 3.0 with ○, not less than 1.0 and less than 2.0 with Δ, and less than 1.0 with x.
(Skin Feel During Rinsing—No Friction)

A composition (1.0 g) was foamed and spread over the whole both hands, and rinsed with a shower of tap water at 35-40° C. while rubbing hands therein for 1 min. Thereafter, frictional feeling was evaluated by 5 panelists.
4: completely no friction
3: almost no friction
2: slight friction
1: rather strong friction
0: extremely strong friction An average point of not less than 3.0 was marked with ⊙, not less than 2.0 and less than 3.0 with ○, not less than 1.0 and less than 2.0 with Δ, and less than 1.0 with x.
(Skin Feel after Use—Silkiness)

A composition (1.0 g) was foamed and spread over the whole both hands, rinsed with a shower of tap water at 35-40° C. while rubbing hands therein for 1 min, and dried with a towel. The skin after drying was evaluated by 5 panelists.
4: extremely silky
3: rather silky
2: normal
1: less silky touch
0: completely no silky touch An average point of not less than 3.0 was marked with ⊙, not less than 2.0 and less than 3.0 with ○, not less than 1.0 and less than 2.0 with Δ, and less than 1.0 with x.
(Emollience (Skin Softness)

A composition (1.0 g) was foamed and spread over the whole both hands, rinsed with a shower of tap water at 35-40° C. while rubbing hands therein for 1 min, and dried with a towel. The skin after drying was evaluated by 5 panelists.
4: no taut feeling, and felt very soft
3: felt soft
2: normal
1: rather taut feeling, and softness was not felt much
0: strong taut feeling, and no softness was felt An average point of not less than 3.0 was marked with ⊙, not less than 2.0 and less than 3.0 with ○, not less than 1.0 and less than 2.0 with Δ, and less than 1.0 with x.

TABLE 1

|   |   | Example 1 | Example 2 | Example 3 | Example 4 | Example 5 | Example 6 | Comp. Ex. 1 | Comp. Ex. 2 | Comp. Ex. 3 | Comp. Ex. 4 | Comp. Ex. 5 |
|---|---|---|---|---|---|---|---|---|---|---|---|---|
| B2 | sodium laureth sulfate | 8.00 | 8.00 | 8.00 | 8.00 | 8.00 | 8.00 | 8.00 | 8.00 | 8.00 | 8.00 | 8.00 |
| C | cocamidopropyl betaine | 4.50 | 4.50 | 4.50 | 4.50 | 4.50 | 4.50 | 4.50 | 4.50 | 4.50 | 4.50 | 4.50 |
| E | 2-hydroxy-1-pentanol | 2.0 | 2.0 | 2.0 | 5.0 | 5.0 | 5.0 | — | — | 2.00 | — | — |
| D | glyceryl caprylate | 1.0 | 5.0 | 5.0 | 5.0 | 5.0 | 5.0 | — | — | — | 1.00 | — |
|   | PEG-30 glyceryl triisostearate | — | — | — | — | — | — | — | — | — | — | 2.00 |
| A | di(phytosteryl/octyldodecyl) lauroyl glutamate | 0.07 | 0.1 | 0.5 | 0.80 | 1.00 | 5.00 | — | 0.07 | 0.02 | 0.02 | 0.5 |
|   | citric acid | pH 6.0 | pH 6.0 | pH 6.0 | pH 6.0 | pH 6.0 | pH 6.0 | pH 6.0 | pH 6.0 | pH 6.0 | pH 6.0 | pH 6.0 |
|   | water | balance | balance | balance | balance | balance | balance | balance | balance | balance | balance | balance |
|   | total (mass %) | 100.00 | 100.00 | 100.00 | 100.00 | 100.00 | 100.00 | 100.00 | 100.00 | 100.00 | 100.00 | 100.00 |
|   | transparency (25° C.) | ⊙ | ⊙ | ⊙ | ⊙ | ⊙ | ○ | ⊙ | X | ⊙ | ⊙ | ○ |
|   | stability (40° C.) | ⊙ | ⊙ | ⊙ | ○ | ○ | ○ | ⊙ | X | X | X | ○ |
|   | foaming property | ⊙ | ⊙ | ⊙ | ○ | ○ | ○ | Δ | X | Δ | ○ | X |
|   | rinsability | ○ | ⊙ | ⊙ | ⊙ | ⊙ | ⊙ | X | X | Δ | Δ | X |
|   | Skin feel during rinsing- no friction | ○ | ○ | ⊙ | ⊙ | ⊙ | ⊙ | ○ | ○ | Δ | Δ | ○ |
|   | Skin feel after use - silkiness | ○ | ○ | ⊙ | ⊙ | ⊙ | ⊙ | X | Δ | Δ | Δ | X |
|   | emollience (skin softness after washing) | ○ | ○ | ○ | ○ | ○ | ○ | X | Δ | Δ | Δ | ○ |

Comparative Example 1 showed good transparency and stability since it does not contain component (A), but was inferior in emollience. However, in Comparative Example 2 in which only component (A) was added to the composition of Comparative Example 1 with the hope of achieving emollience, component (A) was not dispersed stably, transparency and stability were lost, and foaming property was also impaired. In Comparative Example 4 in which only component (D) was further added thereto and Comparative Example 3 in which only component (E) was further added thereto, sufficient stability was not obtained, and satisfactory emollience could not be obtained since the amount capable of solubilizing component (A) was limited. In addition, even when component (A) was solubilized in an aqueous phase by using a nonionic surfactant with high HLB (Comparative Example 5), foaming property and rinsability decreased, and sticky after-use skin feel was produced.

On the other hand, the compositions of Examples, which contain all components (A) to (E), show good transparency, and are superior in stability, with no friction during rinsing, and good emollience. Furthermore, they showed improved foaming property and rinsability, and afforded superior silky touch on the after-use skin.

TABLE 2

|   |   | Example 7 | Example 8 | Example 9 | Example 10 | Comp. Ex. 6 | Comp. Ex. 7 | Comp. Ex. 8 | Comp. Ex. 9 | Comp. Ex. 10 | Comp. Ex. 11 |
|---|---|---|---|---|---|---|---|---|---|---|---|
| B2 | sodium laureth sulfate | 8.00 | 8.00 | 8.00 | 8.00 | 8.00 | 8.00 | 8.00 | 8.00 | 8.00 | 8.00 |
| C | cocamidopropyl betaine | 4.50 | 4.50 | 4.50 | 4.50 | 4.50 | 4.50 | 4.50 | 4.50 | 4.50 | 4.50 |
| E | 2-hydroxy-1-pentanol | 5.0 | — | — | — | — | — | — | — | — | — |
| E | 2-hydroxy-1-hexanol | — | 5.0 | — | — | — | — | — | — | — | — |
| E | 6-hydroxy-1-hexanol | — | — | 5.0 | — | — | — | — | — | — | — |
| E | 3-hydroxy-3-methylbutanol | — | — | — | 5.0 | — | — | — | — | — | — |
|   | 3-hydroxy-1-butanol | — | — | — | — | 5.0 | — | 2.0 | — | — | — |
|   | 2-hydroxypropanol | — | — | — | — | — | 5.0 | 1.0 | — | — | — |
|   | ethanol | — | — | — | — | — | — | — | 5.0 | — | 3.0 |
|   | glycerol | — | — | — | — | — | — | — | — | 5.0 | 10 |
| D | glyceryl caprylate | 5.0 | 5.0 | 5.0 | 5.0 | 5.0 | 5.0 | 5.0 | 5.0 | 5.0 | — |
| A | di(phytosteryl/octyldodecyl) lauroyl glutamate | 0.5 | 0.5 | 0.5 | 0.5 | 0.5 | 0.5 | 0.5 | 0.5 | 0.5 | 0.5 |
|   | citric acid | pH 6.0 | pH 6.0 | pH 6.0 | pH 6.0 | pH 6.0 | pH 6.0 | pH 6.0 | pH 6.0 | pH 6.0 | pH 6.0 |
|   | water | balance | balance | balance | balance | balance | balance | balance | balance | balance | balance |
|   | total (mass %) | 100.00 | 100.00 | 100.00 | 100.00 | 100.00 | 100.00 | 100.00 | 100.00 | 100.00 | 100.00 |
|   | transparency (25° C.) | ⊙ | ⊙ | ⊙ | ○ | X | X | X | Δ | X | X |
|   | stability (40° C.) | ⊙ | ⊙ | ⊙ | ○ | X | X | X | X | X | X |
|   | foaming property | ⊙ | ⊙ | ⊙ | ○ | Δ | Δ | Δ | X | X | X |
|   | rinsability | ⊙ | ⊙ | ⊙ | ⊙ | Δ | Δ | Δ | ○ | Δ | Δ |
|   | Skin feel during rinsing- no friction | ⊙ | ⊙ | ⊙ | ⊙ | ○ | ○ | Δ | X | ○ | X |
|   | Skin feel after use - silkiness | ○ | ○ | ○ | ⊙ | X | X | Δ | ○ | X | Δ |
|   | emollience (skin softness after washing) | ○ | ○ | ○ | ○ | Δ | Δ | Δ | X | Δ | Δ |

When 3-hydroxy-1-butanol and/or 2-hydroxypropanol not falling under component (E) were/was used (Comparative Examples 6, 7 and 8), transparency and stability were poor, and a composition satisfactory as a whole could not be obtained.

In addition, even when component (A) was solubilized in an aqueous phase by using ethanol (Comparative Example 9), use of the volatile solvent caused insufficient stability, low foaming property, friction during rinsing and insufficient emollient effect due to a decreased residual amount of a sterol ester on the skin or hair.

TABLE 3

| | | Ex. 11 | Ex. 12 | Ex. 13 | Ex. 14 | Ex. 15 | Ex. 16 | Comp. Ex. 12 | Comp. Ex. 13 |
|---|---|---|---|---|---|---|---|---|---|
| B2 | sodium laureth sulfate | 8.00 | 8.00 | 8.00 | 8.00 | 8.00 | 8.00 | 8.00 | 8.00 |
| B1 | sodium cocoyl glutamate | 1.50 | 1.50 | 1.50 | 1.50 | 1.50 | 1.50 | 1.50 | 1.50 |
| C | cocamidopropyl betaine | 4.50 | 4.50 | 4.50 | 4.50 | 4.50 | 4.50 | 4.50 | 4.50 |
| E | 2-hydroxy-1-pentanol | 2.0 | 2.0 | 2.0 | 2.0 | 2.0 | 2.0 | 2.0 | 2.0 |
| D | glyceryl caprylate | 5.0 | 5.0 | 5.0 | 5.0 | | | | |
| D | glyceryl caprate | | | | | 5.0 | | | |
| D | glyceryl laurate | | | | | | 5.0 | | |
| | lauric acid BG | | | | | | | 5.0 | |
| | lauric acid PG | | | | | | | | 3.0 |
| | PEG-30 glyceryl triisostearate | | | | | | | | 2.0 |
| A | di(phytosteryl/octyldodecyl/behenyl) lauroyl glutamate | 0.2 | | | | | | | |
| A | phytosteryl N-myristoyl-N-methyl-β-alaninate | | 0.1 | | | | | | |
| A | macadamia nut oil fatty acid phytosteryl ester | | | 0.2 | | | | | |
| A | phytosteryl hydroxystearate | | | | 0.2 | | | | |
| A | di(phytosteryl/octyldodecyl) lauroyl glutamate | | | | | 0.2 | 0.2 | 0.5 | 0.5 |
| | N-myristoyl-N-methyl-β-alanine decyltetradecyl | | 0.1 | | | | | | |
| | citric acid | pH 6.0 | pH 6.0 | pH 6.0 | pH 6.0 | pH 6.0 | pH 6.0 | pH 6.0 | pH 6.0 |
| | water | balance | balance | balance | balance | balance | balance | balance | balance |
| | total (mass %) | 100.00 | 100.00 | 100.00 | 100.00 | 100.00 | 100.00 | 100.00 | 100.00 |
| | transparency (25° C.) | ⊙ | ⊙ | ○ | ○ | ○ | ○ | X | ○ |
| | stability (40° C.) | ⊙ | ⊙ | ○ | ○ | ○ | ○ | X | ○ |
| | foaming property | ⊙ | ⊙ | ○ | ○ | ⊙ | ⊙ | Δ | X |
| | rinsability | ⊙ | ⊙ | ○ | ○ | ⊙ | ⊙ | Δ | X |
| | Skin feel during rinsing- no friction | ○ | ○ | ○ | ○ | ○ | ○ | Δ | ○ |
| | Skin feel after use - silkiness | ○ | ⊙ | ○ | ○ | ○ | ○ | Δ | X |
| | emollience (skin softness after washing) | ⊙ | ⊙ | ○ | ○ | ⊙ | ⊙ | Δ | ⊙ |

The results of Table 3 reveal that the compositions of Examples show good transparency, and are superior in stability, foaming property, rinsability, skin feel (during rinsing and/or after use), and emollience.

The Formulation Examples of the present invention are shown below. It has been revealed that all compositions of the Formulation Examples show good transparency, and are superior in stability, foaming property, rinsability, skin feel (during rinsing and/or after use), and emollience.

TABLE 4

| Formulation Example 1: hair shampoo | (mass %) |
|---|---|
| sodium laureth sulfate | 8.0 |
| cocamidopropyl betaine | 4.5 |
| 2-hydroxy-1-pentanol | 2.0 |
| glyceryl caprylate | 1.0 |
| polysorbate 85 | 1.0 |
| PEG-160 sorbitan triisostearate | 1.0 |
| Polyquaternium 10 | 0.2 |
| di(phytosteryl/octyldodecyl) lauroyl glutamate | 0.5 |
| 10% aqueous citric acid solution | 0.3 |
| water | 81.5 |
| total | 100.0 |
| pH | 6.0 |

TABLE 5

| Formulation Example 2: hair shampoo | (mass %) |
|---|---|
| polyquaternium 10 | 0.2 |
| sodium laureth sulfate | 9.5 |
| cocamidopropyl betaine | 4.5 |
| PEG-7 glyceryl cocoate | 2.0 |
| 2-hydroxy-1-pentanol | 2.0 |
| Sodium PCA | 1.0 |
| triethanolamine cocoyl glutamate | 5.0 |
| di(phytosteryl/octyldodecyl) lauroyl glutamate | 0.2 |
| glyceryl caprylate | 1.0 |
| butyleneglycol laurate | 0.8 |
| magnesium chloride 6 hydrate | 0.2 |
| 20% aqueous citric acid solution | 0.80 |
| water | 72.8 |
| total | 100.0 |
| pH | 5.2 |

TABLE 6

| Formulation Example 3: body shampoo | (mass %) |
|---|---|
| cocoyl alanine triethanolamine | 2.7 |
| lauramidopropyl hydroxysultaine | 4.5 |
| glyceryl caprate | 1.5 |
| PEG-160 sorbitan triisostearate | 0.4 |
| 2-hydroxy-1-hexanol | 1.5 |
| sodium chloride | 0.5 |
| polysorbate 85 | 2.0 |
| di(phytosteryl/octyldodecyl) lauroyl glutamate | 0.5 |
| 20% aqueous citric acid solution | 1.1 |
| water | 85.3 |
| total | 100.0 |
| pH | 6.0 |

TABLE 7

| Formulation Example 4: hair shampoo | (mass %) |
|---|---|
| triethanolamine cocoyl glutamate | 6.00 |
| cocamidopropyl betaine | 4.50 |
| lauryl sulfosodium acetate | 3.00 |
| glyceryl caprylate | 2.00 |
| Sodium PCA | 0.50 |
| 6-hydroxy-1-hexanol | 2.00 |
| di(phytosteryl/octyldodecyl) lauroyl glutamate | 0.30 |
| ceteareth-60 myristyl glycol | 1.00 |
| guar hydroxypropyltrimonium chloride | 0.04 |
| 20% aqueous sodium hydroxide solution | 0.80 |
| water | 79.86 |
| total | 100.00 |
| pH | 5.8 |

TABLE 8

| Formulation Example 5: hair shampoo | (mass %) |
|---|---|
| Polyquaternium 10 | 0.4 |
| triethanolamine cocoyl glutamate | 12.0 |
| cocoyl alanine triethanolamine | 1.8 |
| cocamidopropyl betaine | 0.6 |
| sodium cocoamphoacetate | 0.6 |
| 6-hydroxy-1-hexanol | 2.0 |
| di(phytosteryl/octyldodecyl) lauroyl glutamate | 0.5 |
| sodium PCA | 0.5 |
| glyceryl caprate | 5.0 |
| PEG-150 distearate | 1.0 |
| glycol distearate | 1.0 |
| 20% aqueous citric acid solution | 1.5 |
| magnesium chloride 6 hydrate | 0.6 |
| water | 72.5 |
| total | 100.0 |
| pH | 5.3 |

TABLE 9

| Formulation Example 6: facial wash cream | (mass %) |
|---|---|
| disodium cocoyl glutamate | 5.0 |
| sodium cocoyl threonine | 1.5 |
| cocobetaine | 0.6 |
| sodium lauroamphoacetate | 0.5 |
| glyceryl caprylate | 2.5 |
| Sodium PCA | 0.5 |
| di(phytosteryl/octyldodecyl) lauroyl glutamate | 2.0 |
| Lauroyl lysin | 0.5 |
| 20% aqueous citric acid solution | 3.5 |
| 2-hydroxy-1-pentanol | 2.0 |
| 3-hydroxy-1-propanol | 8.0 |
| guar gum | 0.2 |
| xanthan gum | 0.6 |
| water | 72.6 |
| total | 100.0 |
| pH | 5.8 |

While the hair shampoo of Formulation Example 5 looks white with pearl, this is caused by the precipitation of glycol distearate, and a formulation without glycol distearate is transparent.

While the facial wash cream of Formulation Example 6 is cloudy, this is caused by the dispersion of lauroyl lysin, and a formulation without lauroyllysin is transparent.

The materials used for the present invention are as follows.
Component (A)
di(phytosteryl/octyldodecyl) lauroyl glutamate: "Eldew" PS-203 manufactured by Ajinomoto Co., Inc.
di(phytosteryl/octyldodecyl/behenyl) lauroyl glutamate: "Eldew" PS-304 manufactured by Ajinomoto Co., Inc.
phytosteryl N-myristoyl-N-methyl-β-alaninate: "Eldew" APS-307 manufactured by Ajinomoto Co., Inc. (1:1 by mass mixture of phytosteryl N-myristoyl-N-methyl-β-alaninate and N-myristoyl-N-methyl-β-alanine decyltetradecyl).
macadamia nut fatty acid phytosteryl ester: YOFCO MAS manufactured by Nippon Fine Chemical Co., Ltd.
phytosteryl hydroxystearate: phytosteryl hydroxystearate manufactured by Nikko Chemicals
Component (B)
sodium laureth sulfate: EMAL E-27C manufactured by Kao Corporation
sodium cocoyl glutamate: "Amisoft" CS-22 manufactured by Ajinomoto Co., Inc.
Component (C)
cocamidopropyl betaine: AMPHITOL 55B manufactured by Kao Corporation
Component (D)
glyceryl caprylate: Sunsoft No. 700P-2 manufactured by Taiyo Kagaku Corporation
glyceryl caprate: Sunsoft No. 760 manufactured by Taiyo Kagaku Corporation glyceryl laurate: Sunsoft No. 750 manufactured by Taiyo Kagaku Corporation Component (E)

2-hydroxy-1-pentanol: diol PD manufactured by Kokyu Alcohol Kogyo Co., Ltd.

2-hydroxy-1-hexanol: KMO-6 manufactured by Osaka Organic Chemical Industry Ltd.

6-hydroxy-1-hexanol: 1,6-hexanediol manufactured by Merck 3-hydroxy-3-methylbutanol: isopreneglycol manufactured by KURARAY CO., LTD.

INDUSTRIAL APPLICABILITY

According to the present invention, a composition, particularly a composition for washing, containing a sterol ester, which is an oil poorly soluble in water, and superior in transparency, stability, foaming property, rinsing performance, skin feel (during rinsing and/or after use), and emollience can be provided.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A composition, comprising:
   (A) at least one sterol ester;
   (B) one or more anionic surfactants selected from (B1) N-acylamino acid having a $C_{8-22}$ acyl group or a salt thereof, and (B2) polyoxyethylene alkyl ether sulfate or a salt thereof;
   (C) at least one betaine-type amphoteric surfactant;
   (D) at least one glyceryl mono-$C_{8-14}$ fatty acid ester;
   (E) at least one $C_{5-6}$ hydroxyalcohol; and
   (F) water, and
   having a pH of 4.0 to 8.0.

2. The composition according to claim 1, wherein (A) is at least one N-acylamino acid sterol ester.

3. The composition according to claim 1, wherein (A) is at least one N-acylamino acid sterol ester represented by formula (1):

$$\underset{XOC}{\overset{O}{\|}}-(CH_2)n-\underset{H}{\overset{R^3}{\underset{|}{C}}}-\underset{}{\overset{R^1}{\underset{|}{N}}}-\overset{O}{\overset{\|}{C}}R^2 \quad (1)$$

wherein
X is a hydrogen atom, an ester-forming residue of a $C_{8-38}$ aliphatic alcohol, or an ester-forming residue of a sterol;
$R^1$ is a hydrogen atom or a $C_{1-6}$ alkyl group;
$COR^2$ is a $C_{8-22}$ acyl group;
$R^3$ is a hydrogen atom or a group represented by —COOY, wherein Y is a hydrogen atom, an ester-forming residue of a $C_{8-38}$ aliphatic alcohol, or an ester-forming residue of a sterol; and
n is 1 or 2,
provided that:
when $R^3$ is a hydrogen atom, then X is an ester-forming residue of a sterol, and
when $R^3$ is a group represented by —COOY, then at least one of X and Y is an ester-forming residue of a sterol.

4. The composition according to claim 3, wherein said ester-forming residue of a sterol is an ester-forming residue of phytosterol or cholesterol, $COR^2$ is a lauroyl group or a myristoyl group, and n is 2.

5. The composition according to claim 3, wherein the ester-forming residue of a sterol is an ester-forming residue of phytosterol, $COR^2$ is a lauroyl group, and n is 2.

6. The composition according to claim 1, wherein (A) is at least one member selected from the group consisting of:
   phytosteryl N-myristoyl-N-methyl-β-alaninate;
   di(cholesteryl/behenyl/2-octyldodecyl) N-lauroyl-L-glutamate;
   di(phytosteryl/behenyl/2-octyldodecyl) N-lauroyl-L-glutamate;
   di(cholesteryl/2-octyldodecyl) N-lauroyl-L-glutamate;
   di(phytosteryl/2-octyldodecyl) N-lauroyl-L-glutamate; and
   di(phytosteryl/behenyl/2-octyldodecyl/isostearyl) N-lauroyl-L-glutamate.

7. The composition according to claim 1, wherein (A) is at least one fatty acid sterol ester.

8. The composition according to claim 1, wherein (A) is at least one member selected from the group consisting of phytosteryl butyrate, phytosteryl nonanoate, cholesteryl stearate, cholesteryl isostearate, phytosteryl isostearate, cholesteryl hydroxystearate, phytosteryl hydroxystearate, phytosteryl caprylate/caprate, phytosteryl linoleate, phytosteryl linolenate, phytosteryl ricinoleate, cholesteryl oleate, phytosteryl oleate, dihydrocholesteryl oleate, branched fatty acid ($C_{12-31}$) phytosteryl ester, a phytosteryl canola oil fatty acid glyceride, a phytosteryl rapeseed glyceride, jojoba oil fatty acid phytosteryl ester, Macadamia nut oil fatty acid phytosteryl ester, macadamia nut oil fatty acid cholesteryl ester, macadamia nut oil fatty acid dihydrocholesteryl ester, sunflower seed oil fatty acid phytosteryl ester, rice bran oil fatty acid phytosteryl ester, phytosteryl/isostearyl/cetyl/stearyl/behenyl dimer dilinoleate, bis-behenyl/isostearyl/phytosteryl dimer dilinoleyl dimer dilinoleate, phytosteryl/behenyl dimer dilinoleate, and phytosteryl isostearyl dimer dilinoleate.

9. The composition according to claim 1, wherein (B1) is at least one N-acylamino acid represented by formula (2):

$$R^4CON-\underset{R^6}{\overset{R^5}{\underset{|}{\overset{|}{C}}}}-H-(CH_2)_m-COOH \quad (2)$$

wherein:
$R^4CO$ is a $C_{8-22}$ acyl group;
$R^5$ is a hydrogen atom or a $C_{1-6}$ alkyl group;
$R^6$ is a hydrogen atom, a $C_{1-5}$ alkyl group optionally substituted by a hydroxyl group, or a carboxyl group; and
m is an integer of 0 to 2,
or a salt thereof.

10. The composition according to claim 1, wherein (C) is at least one amide betaine-type amphoteric surfactant represented by formula (4):

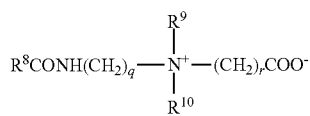 (4)

wherein:
R$^8$CO is a C$_{8-24}$ acyl group;
R$^9$ and R$^{10}$ are each independently a hydrogen atom or a C$_{1-6}$ alkyl group;
q is an integer of 2 to 4; and
r is an integer of 1 to 3.

11. The composition according to claim 1, wherein (D) is glyceryl monocaprylate.

12. The composition according to claim 1, wherein (E) is 2-hydroxy-1-pentanol.

13. The composition according to claim 1, wherein (A) is present in an amount of 0.02 to 5 mass % relative to the total amount of (A)-(F).

14. The composition according to claim 1, wherein (B) is present in an amount of 2 to 35 mass % relative to the total amount of (A)-(F).

15. The composition according to claim 1, wherein (C) is present in an amount of 0.2 to 20 mass % relative to the total amount of (A)-(F).

16. The composition according to claim 1, wherein (D) is present in an amount of 0.1 to 10 mass % relative to the total amount of (A)-(F).

17. The composition according to claim 1, wherein (E) is present in an amount of 0.1 to 10 mass % relative to the total amount of (A)-(F).

18. The composition according to claim 1, wherein (A) and (D) are present in a mass ratio, mass of (A)/mass of (D), of 0.002 to 5.0.

19. The composition according to claim 1, wherein (A) and (E) are present in a mass ratio, mass of (A)/mass of (E), of 0.002 to 5.0.

20. The composition according to claim 1, wherein (A) and the total of (D) and (E) are present in a mass ratio, mass of (A)/(mass of (D)+mass of (E)), of 0.001 to 2.5.

21. The composition according to claim 1, wherein the total of (D) and (E) and the total of (B) and (C) are present in a mass ratio, (mass of (D)+mass of (E))/(mass of (B)+mass of (C)), of 0.003 to 5.0.

22. The composition according to claim 1, which is in a form of a liquid cleanser for skin or hair.

23. A method of stabilizing a composition comprising a sterol ester, a surfactant, and water, said method comprising mixing at least one glyceryl mono-C$_{8-14}$ fatty acid ester and at least one C$_{5-6}$ hydroxyalcohol with said composition.

24. A method of solubilizing a sterol ester in a composition comprising a surfactant and water, said method comprising mixing at least one glyceryl mono-C$_{8-14}$ fatty acid ester and at least one C$_{5-6}$ hydroxyalcohol with said composition.

25. A method of cleansing skin or hair, comprising applying an effective amount of a composition according claim 1 to said skin or hair.

* * * * *